US010010321B2

United States Patent
Cocaign et al.

(10) Patent No.: US 10,010,321 B2
(45) Date of Patent: Jul. 3, 2018

(54) ADJUSTABLE FORCEPS FOR OSTEOSYNTHESIS CLIP

(71) Applicant: Stryker European Holdings I, LLC, Kalamazoo, MI (US)

(72) Inventors: Mael Cocaign, La Riche (FR); Loïc Girod, Goven (FR); Flora Peyret, Rennes (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 123 days.

(21) Appl. No.: 14/400,443

(22) PCT Filed: Mar. 13, 2013

(86) PCT No.: PCT/IB2013/052000
§ 371 (c)(1),
(2) Date: Nov. 11, 2014

(87) PCT Pub. No.: WO2014/140692
PCT Pub. Date: Sep. 18, 2014

(65) Prior Publication Data
US 2016/0000434 A1    Jan. 7, 2016

(51) Int. Cl.
*A61B 17/068* (2006.01)
*A61B 17/064* (2006.01)
(Continued)

(52) U.S. Cl.
CPC ...... *A61B 17/0684* (2013.01); *A61B 17/0642* (2013.01); *A61B 17/0682* (2013.01);
(Continued)

(58) Field of Classification Search
CPC ............ A61B 17/0682; A61B 17/0684; A61B 17/0642; A61B 2017/07235;
(Continued)

(56) References Cited

U.S. PATENT DOCUMENTS 2,222,744 A    11/1940   Gallien, Jr.
3,041,712 A     7/1962   Wurzel
(Continued)

FOREIGN PATENT DOCUMENTS

DE    3337447 A1    5/1985
DE    4110123 A1   10/1992
(Continued)

OTHER PUBLICATIONS

International Search Report and Written Opinion for Application PCT/IB2013/05200 dated Dec. 16, 2013.
(Continued)

*Primary Examiner* — Matthew Lawson
*Assistant Examiner* — Amy Sipp
(74) *Attorney, Agent, or Firm* — Lerner, David, Littenberg, Krumholz & Mentlik, LLP

(57) ABSTRACT

A system and method for the manipulation and insertion of an osteosynthesis clip (100, 200, 300) is provided. The system includes an osteosynthesis clip and an instrument (10). The osteosynthesis clip includes a base (103, 104) having first and second portions, a thickness, and first and second flanges (107, 108) that extend from the base in which the flanges also have a thickness. The instrument of the system includes a distal end (14) and at least a jaw (80), extending from the distal end. The jaw is dimensioned to receive one of the thicknesses of the base and at least one of the flanges. The jaw is movable to a plurality of jaw positions relative to the distal end.

20 Claims, 4 Drawing Sheets

(51) Int. Cl.
*A61B 17/072* (2006.01)
*A61B 17/28* (2006.01)
*A61B 17/29* (2006.01)
*A61B 90/00* (2016.01)

(52) U.S. Cl.
CPC ..... *A61B 17/29* (2013.01); *A61B 2017/07242* (2013.01); *A61B 2017/2845* (2013.01); *A61B 2017/2946* (2013.01); *A61B 2090/0811* (2016.02)

(58) Field of Classification Search
CPC .. A61B 2017/07242; A61B 2017/0725; A61B 2017/0645; A61B 2017/681
USPC .............................. 606/75; 227/175.1, 175.2
See application file for complete search history.

(56) References Cited

U.S. PATENT DOCUMENTS

| | | |
|---|---|---|
| 3,926,195 A | 12/1975 | Bleier et al. |
| 3,960,147 A | 6/1976 | Murray |
| 4,438,769 A | 3/1984 | Pratt et al. |
| 4,462,395 A | 7/1984 | Johnson |
| 4,462,404 A | 7/1984 | Schwarz et al. |
| 4,511,035 A | 4/1985 | Alpern |
| 4,723,540 A | 2/1988 | Gilmer, Jr. |
| 4,841,960 A | 6/1989 | Garner |
| 4,852,558 A | 8/1989 | Outerbridge |
| 4,889,110 A | 12/1989 | Galline et al. |
| 4,957,495 A * | 9/1990 | Kluger ............... A61B 17/7014 606/258 |
| 4,994,063 A | 2/1991 | Garner |
| 5,089,009 A | 2/1992 | Green |
| 5,141,514 A | 8/1992 | van Amelsfort |
| 5,222,975 A | 6/1993 | Crainich |
| 5,242,457 A | 9/1993 | Akopov et al. |
| 5,340,360 A | 8/1994 | Stefanchik |
| 5,342,373 A | 8/1994 | Stefanchik et al. |
| 5,425,489 A | 6/1995 | Shichman et al. |
| 5,439,479 A | 8/1995 | Shichman et al. |
| 5,449,359 A | 9/1995 | Groiso |
| 5,484,451 A | 1/1996 | Akopov et al. |
| 5,660,188 A | 8/1997 | Groiso |
| 5,662,655 A | 9/1997 | Laboureau et al. |
| 5,788,698 A | 8/1998 | Savornin |
| 5,833,697 A | 11/1998 | Ludwick |
| 5,853,414 A | 12/1998 | Groiso |
| 5,941,890 A | 8/1999 | Voegele et al. |
| 5,947,999 A | 9/1999 | Groiso |
| 5,993,476 A | 11/1999 | Groiso |
| 6,261,296 B1 * | 7/2001 | Aebi .................... A61B 17/025 600/219 |
| 6,425,903 B1 | 7/2002 | Voegele |
| 6,446,854 B1 | 9/2002 | Remiszewski et al. |
| 6,635,072 B1 | 10/2003 | Ramamurti et al. |
| 6,685,708 B2 | 2/2004 | Monassevitch et al. |
| 6,716,226 B2 | 4/2004 | Sixto, Jr. et al. |
| 6,726,705 B2 | 4/2004 | Peterson et al. |
| 6,767,356 B2 | 7/2004 | Kanner et al. |
| 6,969,391 B1 | 11/2005 | Gazzani |
| 7,052,504 B2 | 5/2006 | Hughett |
| 7,108,709 B2 | 9/2006 | Cummins |
| 7,112,214 B2 | 9/2006 | Peterson et al. |
| 7,189,234 B2 | 3/2007 | Zucherman et al. |
| 7,211,092 B2 | 5/2007 | Hughett |
| 7,506,791 B2 | 3/2009 | Omaits et al. |
| 7,533,790 B1 | 5/2009 | Knodel et al. |
| 7,547,315 B2 | 6/2009 | Peterson et al. |
| 7,552,853 B2 | 6/2009 | Mas et al. |
| 7,611,038 B2 | 11/2009 | Racenet et al. |
| 7,628,306 B2 | 12/2009 | Spurchise et al. |
| 7,635,367 B2 | 12/2009 | Groiso |
| 7,651,498 B2 | 1/2010 | Shifrin et al. |
| 7,669,747 B2 | 3/2010 | Weisenburgh, II et al. |
| 7,727,245 B2 | 6/2010 | Bender et al. |
| 7,735,703 B2 | 6/2010 | Morgan et al. |
| 7,753,250 B2 | 7/2010 | Clauson et al. |
| 7,766,208 B2 | 8/2010 | Epperly et al. |
| 7,794,475 B2 | 9/2010 | Hess et al. |
| D625,417 S | 10/2010 | Fox et al. |
| 7,811,286 B2 | 10/2010 | Medoff |
| 7,824,426 B2 | 11/2010 | Racenet et al. |
| 7,934,630 B2 | 5/2011 | Shelton, IV et al. |
| 7,942,877 B2 | 5/2011 | Medoff |
| 8,066,720 B2 | 11/2011 | Knodel et al. |
| 8,074,860 B2 | 12/2011 | Yasuda |
| 8,123,101 B2 | 2/2012 | Racenet et al. |
| 8,137,351 B2 | 3/2012 | Prandi |
| 8,186,560 B2 | 5/2012 | Hess et al. |
| 8,211,109 B2 | 7/2012 | Groiso |
| 8,211,126 B2 | 7/2012 | Yeh et al. |
| 8,220,690 B2 | 7/2012 | Hess et al. |
| D669,984 S | 10/2012 | Cheney et al. |
| D669,985 S | 10/2012 | Cheney et al. |
| 8,328,065 B2 | 12/2012 | Shah |
| D675,734 S | 2/2013 | Cheney et al. |
| D676,962 S | 2/2013 | Cheney et al. |
| 8,365,976 B2 | 2/2013 | Hess et al. |
| 8,372,075 B2 | 2/2013 | Groiso |
| D691,720 S | 10/2013 | Cheney et al. |
| D691,722 S | 10/2013 | Cheney |
| 8,584,853 B2 | 11/2013 | Knight et al. |
| D701,307 S | 3/2014 | Protopsaltis et al. |
| D705,930 S | 5/2014 | Cheney |
| D706,927 S | 6/2014 | Cheney et al. |
| D707,357 S | 6/2014 | Cheney et al. |
| 9,034,037 B2 | 5/2015 | Fiere et al. |
| 2002/0029044 A1 | 3/2002 | Monassevitch et al. |
| 2002/0072752 A1 | 6/2002 | Zucherman et al. |
| 2002/0173793 A1 * | 11/2002 | Allen .................. A61B 17/0642 606/75 |
| 2004/0138705 A1 * | 7/2004 | Heino ................... A61B 17/064 606/219 |
| 2005/0049600 A1 | 3/2005 | Groiso |
| 2005/0273108 A1 | 12/2005 | Groiso |
| 2006/0111721 A1 | 5/2006 | Puricelli et al. |
| 2006/0142777 A1 * | 6/2006 | Bastian ................ A61B 17/158 606/88 |
| 2008/0082124 A1 | 4/2008 | Hess et al. |
| 2008/0082125 A1 | 4/2008 | Murray et al. |
| 2008/0161808 A1 | 7/2008 | Fox |
| 2008/0167666 A1 * | 7/2008 | Fiere .................. A61B 17/0642 606/151 |
| 2008/0173691 A1 | 7/2008 | Mas et al. |
| 2008/0173692 A1 | 7/2008 | Spurchise et al. |
| 2008/0177300 A1 | 7/2008 | Mas et al. |
| 2009/0001125 A1 | 1/2009 | Hess et al. |
| 2009/0005807 A1 | 1/2009 | Hess et al. |
| 2009/0018556 A1 * | 1/2009 | Prandi ................ A61B 17/0682 606/151 |
| 2009/0134198 A1 | 5/2009 | Knodel et al. |
| 2009/0242609 A1 | 10/2009 | Kanner |
| 2009/0259249 A1 | 10/2009 | Lobello |
| 2010/0063506 A1 | 3/2010 | Fox et al. |
| 2010/0082030 A1 | 4/2010 | Groiso |
| 2010/0087822 A1 | 4/2010 | Groiso |
| 2010/0133316 A1 | 6/2010 | Lizee et al. |
| 2010/0187283 A1 | 7/2010 | Crainich et al. |
| 2010/0191255 A1 | 7/2010 | Crainich et al. |
| 2010/0237128 A1 | 9/2010 | Miller et al. |
| 2010/0318103 A1 | 12/2010 | Cheng et al. |
| 2011/0087276 A1 | 4/2011 | Bedi et al. |
| 2012/0080336 A1 | 4/2012 | Shelton, IV et al. |
| 2012/0080340 A1 | 4/2012 | Shelton, IV et al. |
| 2012/0145765 A1 | 6/2012 | Peterson et al. |
| 2012/0228355 A1 | 9/2012 | Combrowski et al. |
| 2013/0026206 A1 | 1/2013 | Fox |
| 2013/0030438 A1 | 1/2013 | Fox |
| 2013/0153627 A1 | 6/2013 | Euteneuer et al. |
| 2013/0153628 A1 | 6/2013 | Euteneuer |
| 2013/0231667 A1 * | 9/2013 | Taylor ................ A61B 17/8085 606/75 |

(56) References Cited

U.S. PATENT DOCUMENTS

2014/0018809 A1   1/2014  Allen
2014/0058464 A1*  2/2014  Hutchens ........... A61B 17/7086
                                                            606/86 A
2014/0097228 A1   4/2014  Taylor et al.

FOREIGN PATENT DOCUMENTS

| DE | 19725597 A1 | 10/1998 |
| DE | 212008000029 U1 | 12/2009 |
| EP | 0826340 A2 | 3/1998 |
| EP | 1504723 A2 | 2/2005 |
| FR | 1080876 A | 12/1954 |

OTHER PUBLICATIONS

International Search Report and Written Opinion, PCT/FR2005/050245, dated Sep. 29, 2005.

\* cited by examiner

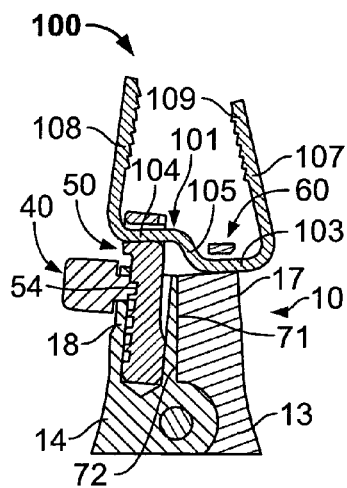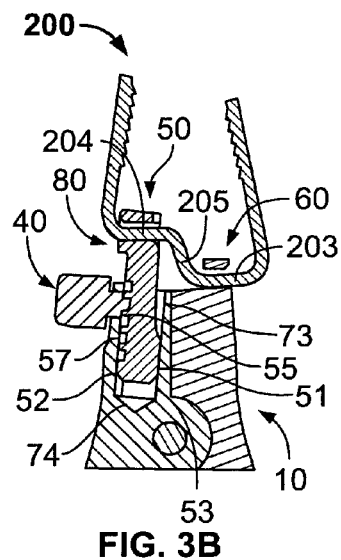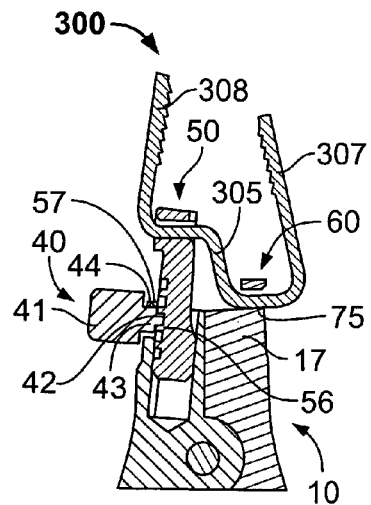
FIG. 3A  FIG. 3B  FIG. 3C
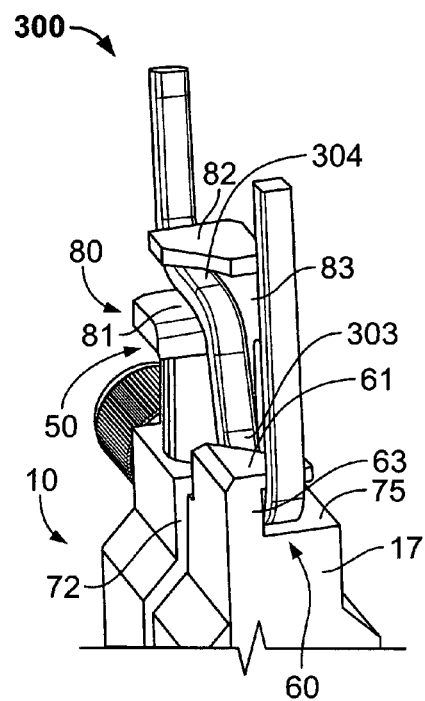
FIG. 4

ADJUSTABLE FORCEPS FOR OSTEOSYNTHESIS CLIP

CROSS-REFERENCE TO RELATED APPLICATIONS

The present application is a national phase entry under 35 U.S.C. § 371 of International Application No. PCT/IB2013/052000 filed Mar. 13, 2013, published as International Publication No. WO 2014/140692 A1, the disclosure of which is hereby incorporated herein by reference.

FIELD OF THE INVENTION

The present invention relates to surgical tools for treatment of patients requiring osteosynthesis, and more particularly to tools for the insertion of stepped osteosynthesis clips.

BACKGROUND OF THE INVENTION

A displacement osteotomy procedure may be performed to correct misalignment of bones and joints. This technique is often used in the calcaneus when heel valgus or varus conditions are present, which are frequently associated with pes planus, i.e., flat foot, or with pes cavus, i.e., high arch foot. For such conditions, a displacement osteotomy is used for medializing for flatfoot or lateralizing for pes cavus to enable a surgeon, or other qualified person, to reposition the heel and realign it with the longitudinal axis of the tibia, eventually leading to correction of the associated foot deformity. Stepped osteosynthesis clips are often used for performing osteosynthesis in connection with these procedures. These stepped clips are often in the form of a staple having an offset crown or base and a pair of opposing legs or flanges extending from the crown. Stepped staples allow for quick and easy bone fixation, are minimally invasive, and have low complication rates. FIG. 1 is an example of the use of stepped staples. In this example, two staples 1 have been inserted into adjacent anterior and posterior portions 3, 4 of a severed calcaneus bone. As shown, the posterior portion 4 of the bone is offset.

Superelastic staples made of nitinol alloy have been in use for more than two decades in the orthopaedic field. Typically, these staples are in a normally closed position when no constraints, such as external forces or temperature changes, are applied. Thus, forceps or clamps that apply and maintain a load to the legs of an osteosynthesis clip until the legs are in an open, generally parallel, position are commonly used to insert these staples into pre-drilled holes during an osteotomy procedure. One example of these types of forceps is discussed in U.S. Pat. No. 8,137,351, the disclosure of which is hereby incorporated by reference herein. Current designs of clamps for osteosynthesis staples are adaptable to different widths of the crowns and lengths of the legs of staples. However, current forceps are not designed for use with clips having an offset crown.

Therefore, there is a need to provide a device that is operable with stepped osteosynthesis clips having an offset crown.

BRIEF SUMMARY OF THE INVENTION

In accordance with an embodiment, an instrument for the manipulation and insertion of an osteosynthesis clip may be provided. The osteosynthesis clip may include a base having a thickness and may include at least first and second flanges. The first and second flanges may extend from the base and may have a thickness.

The instrument may include a first distal end. The instrument may include a second distal end attached to the first distal end. The instrument may include a jaw assembly. The jaw assembly may extend from the second distal end. The jaw assembly may be dimensioned to receive one of the thicknesses of the base and at least one of the flanges. The jaw assembly may be movable to a plurality of positions relative to the second distal end.

In some arrangements, the instrument may include a first arm. The first arm may include the first distal end. The instrument may include a second arm. The second arm may be attached to the first arm and may include the second distal end. The respective first and second distal ends of the first and second arms may be separable to a plurality of arm positions from each other.

Continuing with this embodiment, at least a first jaw may be attached to the first distal end. The first jaw may be dimensioned to receive the thickness of at least one of the first portion of the base and the first flange. The jaw assembly may include at least a pair of second jaws may extend from the second distal end. The pair of second jaws may be dimensioned to receive the thickness of at least one of the second portion of the base and the second flange. The pair of second jaws may be moveable to the plurality of positions relative to the second distal end.

In some arrangements, the plurality of positions of the pair of second jaws may include at least first and second positions. In some arrangements, the pair of second jaws may be moveable to at least first and second positions when the respective first and second distal ends of the first and second arms are separated by any of the plurality of arm positions.

In some arrangements, the first and second arms may be connected and may be pivotal about a joint. In some such arrangements, the respective first and second distal ends of the first and second arms may be separable upon pivotal movement about the joint.

In some arrangements, the second distal end may have a bore. The bore may extend at least partially into the second distal end. In some arrangements, a post may be slideable within the bore. In some such arrangements, the pair of second jaws may extend from the post.

In some arrangements, a post may be extendable from the second distal end. In some such arrangements, the pair of second jaws may be attached to the post. In some arrangements, a fastener may be attached to the second distal end. In some arrangements, the fastener may be moveable from a first position to a second position in a direction transverse to the movement of the pair of second jaws. In some arrangements, the fastener may not be engaged with the post in the first position of the fastener such that the post may be extendable from the second distal end. In some arrangements, the fastener may be engaged with the post in the second position of the fastener such that the post is not extendable from the second distal end.

In some arrangements, the post may include at least one notch. In some such arrangements, a distal end of the fastener may be dimensioned to be received in the one or more notches to set the post at a predetermined location relative to the second distal end.

In some arrangements, the instrument may include a post which may extend from the second distal end. In some such arrangements, the pair of second jaws may be attached to the post. In some arrangements, the instrument may include an adjustment mechanism for engagement with a post. In some such arrangements, the post may be in a first post position at a first position of the adjustment mechanism and may be in a second post position at a second position of the adjustment mechanism.

In some arrangements, the instrument may include a post that may extend from the second distal end. In some such arrangements, a measurement marker may be placed on the post. In some arrangements, the pair of second jaws may be attached to the post. In some such arrangements, the measurement marker may provide a marker for determining the relative location of one or both of the post and the pair of second jaws to the second distal end.

In some arrangements, the first jaw attached to the first distal end may define a first channel. In some arrangements, the pair of second jaws extending from the second distal end may define a second channel. In some arrangements, the first and second channels may face in opposite directions. In some arrangements, the first and second channels may receive the thickness of the one or more of the first and second portions of the base and the first and second flanges.

In accordance with another embodiment, a system for the manipulation and insertion of an osteosynthesis clip may be provided. The system may include an osteosynthesis clip and an instrument. The osteosynthesis clip may include a base. The base may have first and second portions. The base may have a thickness and may have at least first and second flanges extending from the base. The flanges may have a thickness.

The instrument may include a first distal end and may include at least a first jaw. The first jaw may extend from the distal end and may be dimensioned to receive one of the thickness of the base and at least one of the flanges. The first jaw may be movable to a plurality of jaw positions relative to the first distal end.

In some arrangements, the instrument may include a first arm. The first arm may include the first distal end. A second arm may be connected to the first arm at a joint. The second arm may include a second distal end and may include at least a second jaw attached to the second distal end. The second jaw may be dimensioned to receive the thickness of at least one of the first portion of the base and the first flange of the at least one osteosynthesis clip. In some arrangements, the first and second arms may be pivotal to separate the first and second distal ends from each other. In some arrangements, the first and second portions of the base may be offset from each other prior to being received in the first jaw and the second jaw, respectively. In some arrangements, the osteosynthesis clip may be a stepped staple.

In some arrangements, the system may include a plurality of osteosynthesis clips. In some arrangements, the first and second portions of the base of a first clip may be offset from each other a first distance prior to being received in the first jaw and the second jaw, respectively. In some arrangements, the first and second portions of the base of a second clip may be offset from each other a second distance different than the first distance prior to being received in the first jaw and the second jaw, respectively.

In some arrangements, profiles of each of the first and second flanges of the osteosynthesis clip and the first and second arms may lie in the same plane. In some arrangements, such profiles may lie in the same plane when one or both of the first portion of the base and the first flange are received in the first jaw. In some arrangements, such profiles may lie in the same plane when one or both of the second portions of the base and the second flange are received in the second jaw.

In some arrangements, the first distal end may have a bore. In some such arrangements, the bore may extend into the first distal end. In some such arrangements, the system may include a post which may be slideable within the bore. In some such arrangements, the first jaw may extend from the post.

In some arrangements, the system may include a post and may include a fastener. In some such arrangements, the post may be extendable from the first distal end. In some such arrangements, the first jaw may be attached to the post. In some arrangements, the fastener may be attached to the first distal end. In some arrangements, the fastener may be moveable from a first position to a second position in a direction transverse or substantially transverse to the movement of the first jaw. In some arrangements, the fastener may not be engaged with the post in the first position of the fastener such that the post may be extendable from the first distal end. In some arrangements, the fastener may be engaged with the post in the second position of the fastener such that the post may not be extendable from the first distal end. In some such arrangements, the post may include at least one notch. In some such arrangements, the distal end of the fastener may be dimensioned to be received in the one or more notches. In some arrangements, the post may be set at a predetermined location relative to the first distal end when the fastener is received in the one or more notches.

In accordance with an embodiment, a system for the manipulation and insertion of an osteosynthesis clip may be provided. The system may include at least one osteosynthesis clip and an instrument. The osteosynthesis clip may include a base having at least first and second portions. The osteosynthesis clip may have a thickness and may have at least first and second flanges extending from the base. The first and second flanges may have a thickness.

The instrument may include a pair of arms connected at a joint. Each of the pair of arms may have first and second distal ends, respectively. The pair of arms may be pivotal to separate the first and second distal ends from each other. The instrument may include at least a first jaw. The first jaw may be attached to the first distal end and may be dimensioned to receive the thickness of at least one of the first portion of the base and the first flange of the one or more osteosynthesis clips. The instrument may include at least a pair of second jaws. The pair of second jaws may be attached to the second prong and may be dimensioned to receive the thickness of at least one of the second portion of the base and the second flange of the one or more osteosynthesis clips. The pair of second jaws may be moveable to at least first and second jaw positions relative to the second distal end.

In some arrangements, the instrument may include a post. In some arrangements, the post may be extendable from the first distal end. In some arrangements, the first jaw may be attached to the post. In some arrangements, the instrument may include an adjustment mechanism for engagement with the post. In some such arrangements, the post may be in a first position at a first position of the adjustment mechanism. In some such arrangements, the post may be in a second position at a second position of the adjustment mechanism.

In some arrangements, the second portion of the base of the osteosynthesis clip may be closer to the first portion of the base of the osteosynthesis clip when the first jaw is in the first jaw position than when the first jaw is in the second jaw position.

In accordance with another embodiment, an instrument for the manipulation and insertion of an osteosynthesis clip may be provided. The osteosynthesis clip may include a base. The base may have at least first and second portions.

The base may have a thickness and may have at least first and second flanges. The first and second flanges may extend from the base and may have a thickness. The instrument may include a first arm. The first arm may have a first distal end. The instrument may include a second arm. The second arm may be attached to the first arm and may have a second distal end. The respective distal ends of the first and second arms may be separable to a plurality of arm positions from each other.

Continuing with this embodiment, at least a first jaw may be attached to the first distal end. The first jaw may be dimensioned to receive the thickness of at least one of the first portion of the base and the first flange. At least a pair of second jaws may extend from the second distal end. The pair of second jaws may be dimensioned to receive the thickness of at least one of the second portion of the base and the second flange. The pair of second jaws may be moveable to a plurality of positions relative to the second distal end.

In accordance with another embodiment, a method for preparing an osteosynthesis clip for insertion into bone tissue is provided. In one step, an osteosynthesis clip may be provided. The osteosynthesis clip may include a base. The base may have at least first and second portions. The base may have a thickness and may have at least first and second flanges. The flanges may extend at an angle from the base. The flanges may have a thickness. In another step, an instrument may be provided. The instrument may have at least first and second jaws. In another step, a first portion of the base may be received into a first channel. The first channel may be defined by at least the first jaw attached to a first arm on a first distal end thereof. In another step, the second jaw may be adjusted to one of a plurality of positions. The second jaw may define a second channel and may be attached to a second arm on a second distal end of the arm. The distal ends of the first and second arms may be separable to separate the prongs by at least both of first and second distances from each other. In another step, the second portion of the base may be received into the second channel in the one of the plurality of positions.

In accordance with another embodiment, a method for preparing an osteosynthesis clip for insertion into tissue is provided. In one step, a plurality of osteosynthesis clips is provided. Each of the osteosynthesis clips may include a base. The base of each of the plurality of osteosynthesis clips may have a thickness and a different offset than the offset of the other of the plurality of osteosynthesis clips. The plurality of the osteosynthesis clips may have at least first and second flanges extending from the base and may have a thickness. In another step, an instrument may be provided. The instrument may have a first distal end. The first distal end may include at least a first jaw. The instrument may include a second distal end. The second distal end may include at least a second jaw. The second jaw may be adjustable to a plurality of positions relative to the second distal end. In another step, one osteosynthesis clip of the plurality of osteosynthesis clips may be selected. In another step, the second jaw may be adjusted to one of the plurality of positions relative to the offset of the selected osteosynthesis clip. The second jaw may be adjustable relative to the offset of each of the plurality of osteosynthesis clips. In another step, the osteosynthesis clip selected may be positioned at the first and second distal ends of the instrument. The first and second jaws may engage at least a portion of the base of the clip.

BRIEF DESCRIPTION OF THE DRAWINGS

FIGS. 3(A)-(C) are cross-sectional plan views of a portion of a system in accordance with an embodiment, the system including the instrument of FIG. 2, a portion of which is illustrated.

FIG. 4 is a perspective view of the portion of the system illustrated in FIG. 3(C).

DETAILED DESCRIPTION

Where reference is or has been made herein to directional terms such as "proximal," "proximal most," "distal," and "distal most," it is to be understood that "proximal" and "proximal most" refer to locations closer to a user or operator of the device or method being described and that "distal" and "distal most" refer to locations further from a user or operator of the device or method being described. Where reference is or has been made herein to directional terms such as "anterior," "posterior," "medial," and "lateral," it is to be understood that such terms refer to their common usage relative to human anatomy, i.e., "anterior" and "posterior" refer to relative positions along the anteroposterior axis passing through the front and back of a person, respectively, whereas "medial" and "lateral" refer to relative positions along the mediolateral axis perpendicular to the anteroposterior axis and passing through the center as well as the left and right sides of a person.

Figure 2:
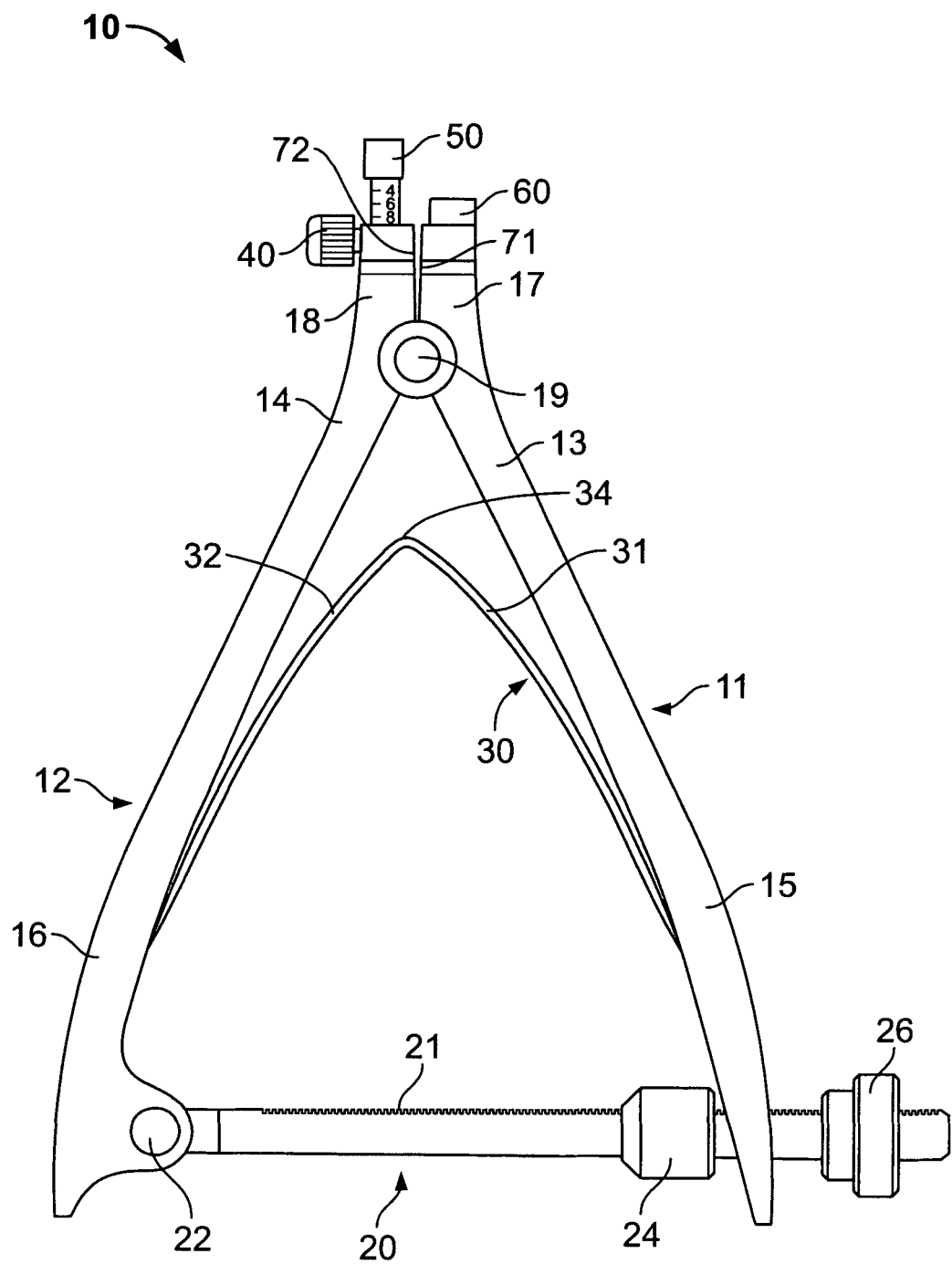
FIG. 2 is a plan view of an instrument for the manipulation and insertion of an osteosynthesis clip in accordance with an embodiment.

Referring to FIG. 2, an instrument 10 may include a first arm 11 and a second arm 12, which may be attached at a joint 19. The joint may be formed by a fastener such as a screw, as shown, or a rivet as well as by other mechanisms of connection known to those of ordinary skill in the art. The joint 19 may be formed on distal ends 13, 14 of each of the respective first and second arms 11, 12 allowing for the first and second arms 11, 12 to pivot about the joint 19 through a plurality of relative angular positions. The first and second arms 11, 12 may include respective first and second prongs 17, 18 at distal-most portions of the respective distal ends 13, 14 of the arms 11, 12.

As shown, the arms 11, 12 may be convex at each of the respective distal ends 13, 14 such that the first and second prongs 17 and 18 thereof may simultaneously extend in the distal direction such that the first and second prongs 17, 18 may be substantially parallel. The arms 11, 12 may be concave at the proximal ends 15, 16, which may provide an easier grip for a user of the instrument 10. As shown the arms 11, 12 may have substantially flat upper and lower surfaces. In alternative arrangements, the arms may be shaped differently such as to have alternative shapes and configurations including but not limited to straight proximal ends, cylindrical cross-sections, and the like.

As further shown in FIG. 2, the instrument 10 may include a rod 20 extending between the first and second arms 11, 12. As shown, a connection joint 22 may attach the rod 20 to the proximal end 16 of the second arm 12, although, in other arrangements, a connection joint may attach the rod to the first arm. The connection joint 22 may be a fastener such as a screw, as shown, or a rivet as well as by other mechanisms of connection known to those of ordinary skill in the art. As shown, the rod 20 may pass through the first arm 11 (or alternatively the second arm 12), such as through a slot (not shown) on the proximal end 15 of the first arm 11, such that the first arm 11 may be moved along and relative to the rod 20. In an alternative arrangement, the rod may have a slot through which the arm may pass to function in the same manner.

An inner stop 24 may be positioned onto the rod 20 between the first and second arms 11, 12. The inner stop 24 may be adjustable to fixed positions along the rod 20 to prevent contact between the respective proximal ends 15, 16 of the first and second arms 11, 12 and to limit a range of motion of the arms. As shown, an outer stop 26 may be positioned onto the rod 20 adjacent to the proximal portion 15 of the first arm 11 and outside of a space between the first and second arms 11, 12, although in alternative arrangements, the outer stop may be positioned adjacent to the proximal portion of the second arm. The outer stop 26 may be adjustable to fixed positions along the rod 20 to prevent movement of the proximal end 15 of the first arm 11 in a direction away from the second arm 12. In this manner, as illustrated, the inner stop 24 and the outer stop 26 may interact on opposite sides of the arm 15 to limit the movement of the arm 15 between the inner stop 24 and the outer stop 26. These stops 24, 26, while limiting movement of arms 15, 16 relative to one another, may also limit one or both of movement and alteration of a clip positioned at the distal prongs 17, 18, as will be discussed further below. In some arrangements, the rod 20 may have threads 21 that run along at least a portion of a length of the rod 20 and one or both of the inner stop 24 and the outer stop 26 may have internal threads running therethrough, respectively such that one or both of the inner stop 24 and the outer stop 26 may be rotated to be translated along the rod 20 to respective fixed positions along the rod 20. In alternative arrangements, the rod may be a rail which may have teeth along at least a portion thereof which may interface with inner and outer stops for engagement therewith.

The instrument 10 may include a compression element 30 which may act against a force applied to one or both of the first and second arms 11, 12 to prevent movement of one or both of the arms 11, 12 in a direction towards the other arm. As shown, such an element may be but is not limited to a leaf spring. The compression element 30 may have first and second compression elements 31, 32, which may be leaves of a leaf spring, that are joined together at a joint 34 at a respective ends of the first and second compression elements 31, 32 and joined to the respective first and second arms 11, 12 against which the compression element may act, respectively.

As further shown in FIG. 2 and in greater detail in FIGS. 3(A)-3C, a first jaw 60 may be engaged with the first prong 17 on the distal end 13 of the first arm 11 and a pressure screw 40 and a post 50 may be engaged with the second prong 18 on the distal end 14 of the second arm 12. Referring to FIGS. 3(A)-3(C), the post 50 may be inserted into a bore 73, which may be a blind hole, extending in a proximal direction from a distal most portion of the prong 18 to a bottom 74 of the bore 73. At least a portion of the post 50 that interfaces with the bore 73 may be cylindrical or, as shown, the post 50 may have a perimeter including at least first and second post surfaces 51, 52 that may slide along the bore 73. In such arrangements, the perimeter of the post 50 may be only slightly smaller than the bore 73 such that the post may be inserted into the bore 73 and not experience any significant angulation or other undesirable relative movement or play. The post 50 may have a post bottom 53 that may abut the bottom 74 of the bore 73 and in this manner may act as a physical hard stop for the post 50. As shown, the post bottom 53 and bottom 74 of the bore 73 may have reciprocal chamfers for engagement with each other and for ease of manufacturing, although in other arrangements, the bottom 74 may be flat along at least a portion thereof to allow for contact with a corresponding flat surface of the post bottom 53.

The post 50 may further include a plurality of notches that may be inset from the second post surface 52, such as the notches 54-56 designated in FIGS. 3(A)-3(C), respectively. As shown in these figures, each of the notches 54-56 may be placed in series along the post 50 in the proximal-distal direction such that the respective notches 54-56 may be associated with a particular size of an osteosynthesis clip, or other similar clip or fastener, as discussed further herein. In some arrangements, as shown, a slot 57 may extend along the post 50 in the proximal-distal direction to provide a step that may be adjacent to and that may surround the notches, such as the notches 54-56.

Still referring to FIGS. 3(A)-(C), an adjustment mechanism 40, such as but not limited to a pressure screw, may be engaged with the post 50 to provide a physical stop for the post 50 in the proximal-distal direction. As shown, the adjustment mechanism 40 may have a handle 41, such as but not limited to a knob, and at least a protrusion 42 that may be inserted into any of the respective notches including the notches designated 54-56, which are used for illustration purposes herein. In some arrangements, as shown, the adjustment mechanism 40 may include a engagement section 43, which may be but is not limited to being a cylindrical step having threads 44 and having a diameter smaller than the diameter of the handle 41 and larger than the diameter of the protrusion 42, as shown, a threaded portion of the protrusion 42, or the protrusion itself in which the protrusion is threaded. In alternative arrangements, the adjustment mechanism may be pressed into and pulled out of the notches without the need for any threads. In any of such arrangements, the slot 57 of the post 50 may be dimensioned such that the protrusion 42 of the adjustment mechanism 40 may slide along the slot 57 to be repositioned among any of the notches without the need to remove the adjustment mechanism 40 from the protrusion 18.

Referring now to FIGS. 3(A)-(C) and 4, clips such as any of clips 100, 200, and 300, which may be osteosynthesis staples as shown, may be inserted into channels defined at least in part by a first jaw 60 and a pair of second jaws 80, as discussed further herein. As in the example of FIG. 3(A), the clip 100 may have first and second flanges 107, 108 extending from respective first and second base portions 103, 104. The first and second flanges may have tines or teeth 109, respectively, extending therefrom. The first and second base portions 103, 104 may be offset from each other and connected by an inner base portion 105 to form a base 101. Each of the clips 100, 200, and 300 may have similar features with the exception that the clip 200 may have an inner base portion 205 that is longer than the inner base portion 105, and the clip 300 may have an inner base portion 305 that is longer than both the inner base portion 105 and the inner base portion 205. In this manner, first and second base portions 304, 305 of the clip 300 may be offset a greater distance than first and second base portions 204, 205 of the clip 200, and similarly, the first and second base portions of the clip 200 may be offset a greater distance than the first and second base portions 104, 105 of the clip 100.

The pair of second jaws 80 may include a second proximal jaw 81 and an opposing second distal jaw 82 that may be joined by a second jaw connector 83. As best shown in FIG. 4, the second proximal jaw 81 and the opposing distal jaw 82 may define an opening through which a thickness of the second base portion 304 of the clip 300, may pass, for example. As further shown in the example of FIG. 4, the second proximal jaw 81, the opposing second distal jaw 82, and the second jaw connector 83 may define a channel for receiving the thickness of second base portion 304 of the clip 300.

As also best shown in the example of FIG. 4, the first jaw 60 may include a first distal jaw 61 and a first prong surface 75 on a distal most end of the prong 17 that may be joined by a first jaw connector 63. Similar to the pair of second jaws 80, the first distal jaw 61 and the first prong surface 75 may define an opening through which a thickness of the first base portion 303 may pass for example. As further shown in the example of FIG. 4, the first distal jaw 61, the first prong surface 75, and the second jaw connector 83 may define a channel for receiving the thickness of the first base portion 303 of the clip 300.

Referring again to FIG. 2, in operation during one embodiment of a method of use, the respective proximal ends 15, 16 of the first and second arms 11, 12 may be separated manually or may be separated due to a compressive force applied by the compression element 30 until inwardly-facing opposing first and second surfaces 71, 72 on the respective prongs 17, 18 of the distal ends 13, 14 contact one another. Now referring to FIGS. 3(A)-(C), in this compressed position, with the adjustment mechanism 40 in a retracted position outside of the bore 73, the post 50 may be set at a position within the bore 73 in order to place the pair of second jaws 80 on the post 50 at a desired distance in a distal direction from the second prong 18 of the second distal end 14 of the second arm 12. Such a position may be determined through the use of a measurement marker 58 that may be located along the post 50 (see FIG. 5(B)). The adjustment mechanism 40 may then be inserted into the appropriate notch, such as any of the notches 54-56 to fix the position of the post 50. In this manner, the desired clip may then be inserted into the pair of second jaws 50 and the first jaw 60, as shown by the examples of FIGS. 3(A)-(C) in which the clips 100, 200, and 300 have been inserted into the instrument 10 when the adjustment mechanism 40 is inserted into the respective notches 54, 55, and 56. Referring to FIG. 4, the channels defined by the pair of second jaws 80 and the first jaw 60 may face in opposite directions such that the instrument 10 may be twisted relative to a clip to be received by the instrument. In this manner, the clip may be held in place by the instrument 10.

Figure 1:
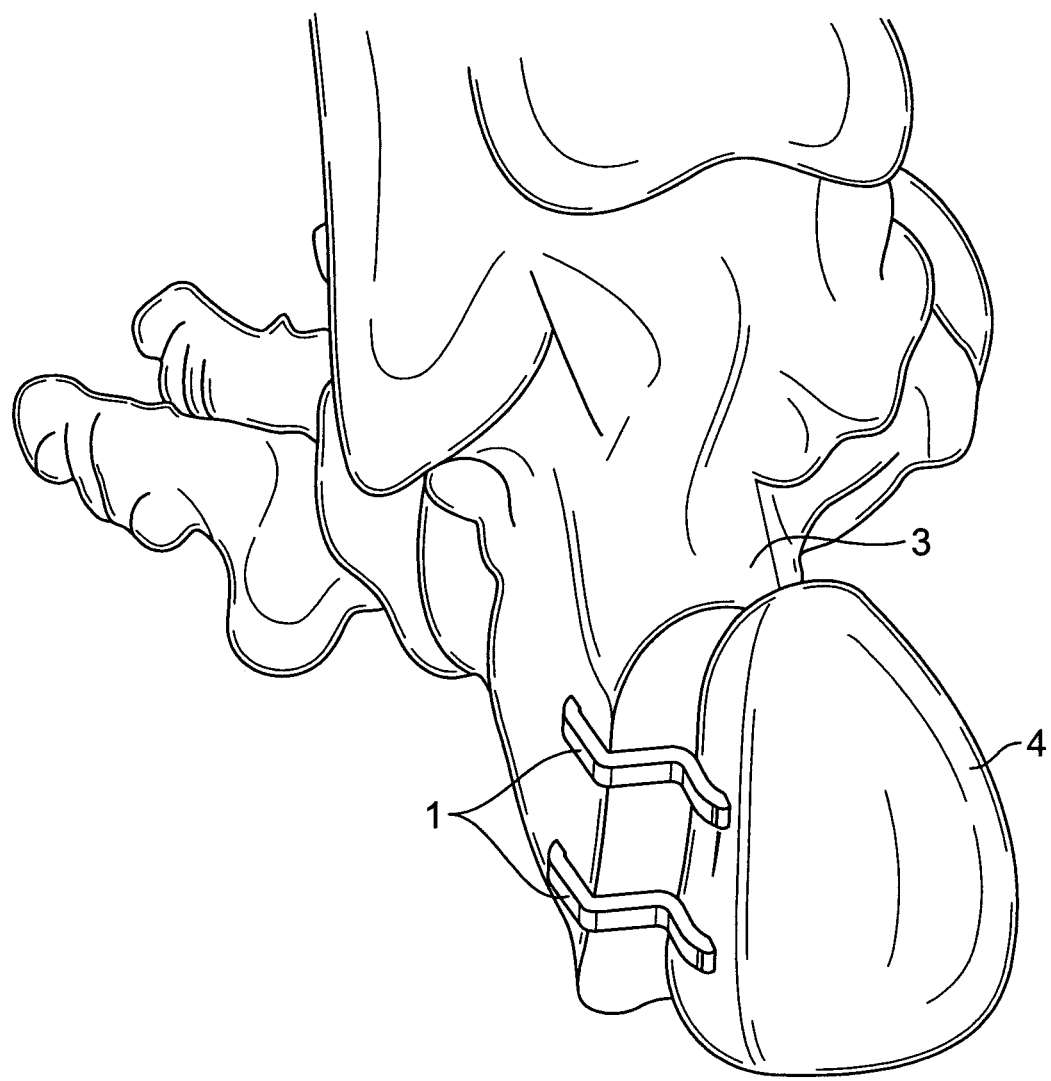
FIG. 1 is a perspective view of a posterior of a foot having a pair of staples inserted therein as known in the prior art.
Figure 5A:
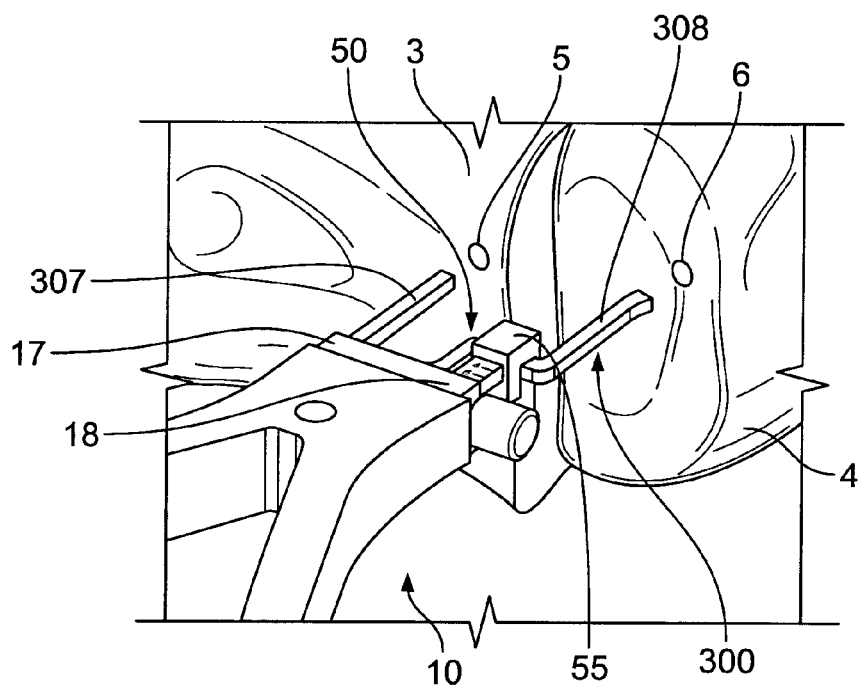
FIGS. 5(A) and 5(B) are perspective views of portions of the system illustrated in FIG. 3(C) and the foot illustrated in FIG. 1 during one embodiment of a use of the system.
Figure 5B:
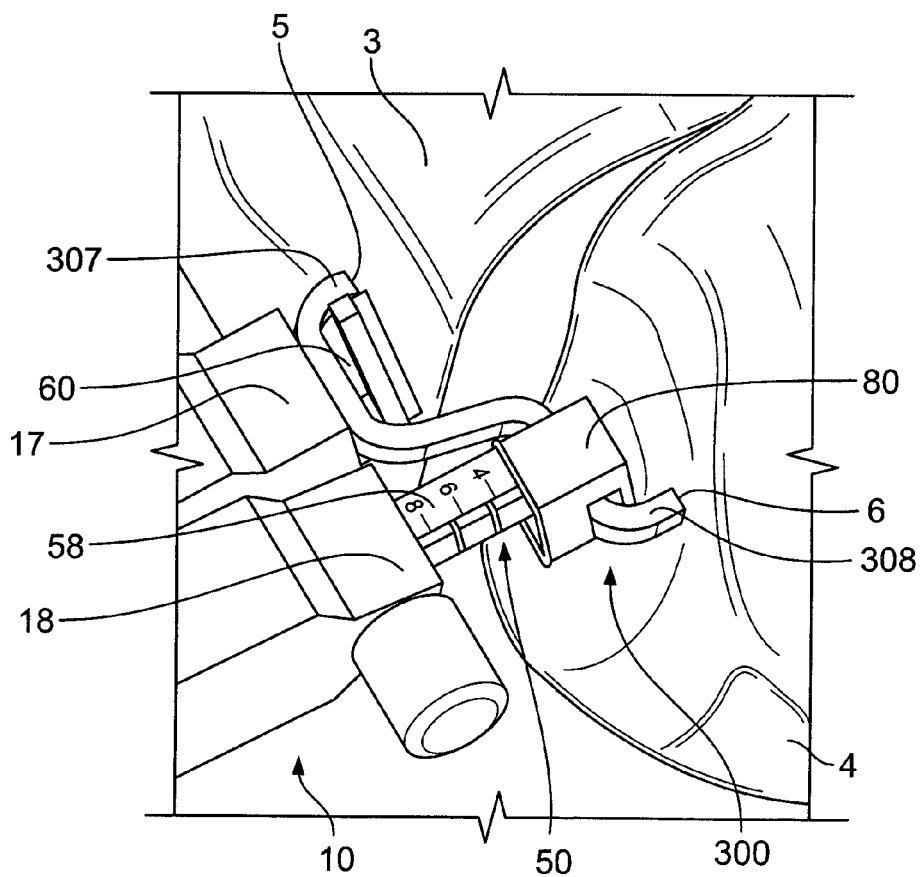

Referring now to FIGS. 1 and 5, after inserting the clip, in this example the clip 300, the inner stop 24 of the instrument 10 may be rotated such that the inner stop 24 translates along the rod 20 towards the second arm 12 to provide clearance for movement of the first arm 11 towards the second arm 12. The first and second arms 11, 12 may then be compressed towards each other at the respective proximal ends 15, 16 thereof to cause the respective prongs 71, 72 to separate. In this manner, the flanges 307, 308 of the clip 300 may be spread apart. During this step, the inner stop 24 and the outer stop 26 may limit the relative movement of the flanges 307, 308 of the clip 300 to avoid breakage or deformation of the clips during opening. Once the flanges 307, 308 are placed into a desirably perpendicular direction with respect to the respective first and second base portions 303, 304, the inner stop 24 and the outer stop 26 may then be rotated to lock the position of the proximal end 15 of the first arm 11 relative to the proximal end 16 of the second arm 12, and thus lock the relative position of first and second arms 11, 12 in light of their connection at the joint 19. As shown in FIG. 5A, holes 5, 6 may be drilled into bone parts or fragments, such as severed portions 3, 4 of the calcaneus of a foot, respectively, though the flanges 307, 308 of clip 300 may have self-tapping distal tips such that pre-drilled holes 5, 6 are not necessary. As next shown in FIG. 5B, the distally-pointing first and second flanges 307, 308 of the clip 300 may then be inserted into the respective holes 5, 6 in the calcaneus. The outer stop 26 may then be rotated to permit the arms 11, 12 to spread apart such that the respective prongs 71, 72 move toward each other. At a predetermined relative position of the prongs 71, 72, the clip 300 may not be tightly held. At such a position, the instrument 10 may be easily separated from the clip 300 by rotating the instrument 10, as shown in a counter clockwise direction, to disengage the instrument from the clip 300 and by moving the instrument away from the clip 300.

In an alternative arrangement to that shown in the figures, the adjustment mechanism may be a gear, such as a worm gear. In such an arrangement, the adjustment mechanism may have a longitudinal axis parallel to a longitudinal axis of the post. The post may have gear teeth that may have corresponding gear teeth to mesh with the adjustment mechanism. In this manner, the adjustment mechanism may be rotated to cause the post to move in the distal and proximal positions relative to the prong. In another alternative arrangement, the adjustment mechanism may be a pinion gear that meshes with gear teeth on the post, such as in a rack and pinion configuration. In still other alternative arrangements, the interface between the adjustment mechanism and the post may be any interface for remotely causing translational movement of an object known to those of ordinary skill in the art.

In another alternative arrangement, any of the jaws described herein may be moveable in directions at an angle with or transverse to the proximal-distal direction to accommodate different shapes and sizes of clips, such as clips having curved, wavy, or other such shapes of bases. For example, each of the pair of second jaws may be translatable in a opposite direction perpendicular to the proximal-distal direction of movement of the post such that the jaws spread apart to allow wider or narrower clips to be placed between the jaws. In some alternative arrangements, either of the prongs described herein may be moveable in directions at an angle with or transverse to the proximal-distal direction.

In another embodiment, the present invention may include a system or kit including instrument 10 and at least one of the clip 100, 200, 300. In a preferred embodiment, the system or kit includes a plurality of clips 100, 200, 300 such that the system or kit includes an assortment of clips having varying sizes and shapes such that the operator may select the proper sized clip for a particular application or use. The adjustment mechanism 40 and the post 50 allow for the single instrument 10 to be used with any of the clips 100, 200, 300 supplied with the system or kit. It should also be understood that clips 100, 200, 300 are merely exemplary sizes and thus clips may be available to an operator in all manner of shapes and sizes other than just those illustrated in and described with respect to FIGS. 3-5.

In an alternative arrangement, such a system or kit may include a plurality of posts that may have different shapes and sizes to accommodate the differently sized clips.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, or a particular claim, that feature can also be used, to the extent possible, in combination with and/or in the context of other particular aspects, arrangements, configurations, and embodiments of the invention, and in the invention generally.

Furthermore, although the invention herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below. Moreover, the foregoing disclosure should be taken by way of illustration rather than by way of limitation as the present invention is defined by the claims set forth below.

The invention claimed is:

1. An instrument for the manipulation and insertion of an osteosynthesis clip, the osteosynthesis clip including a base having a thickness and at least first and second flanges extending from the base and having a thickness, the instrument comprising:
a first arm including a first distal end;
a second arm attached to the first arm and including a second distal end, the second distal end having a blind bore extending therein; and
a jaw assembly extending from the second distal end, the jaw assembly including a post slideable within the blind bore to a plurality of positions relative to the second distal end and at least a pair of second jaws extending from the post and dimensioned to receive either or both of the thicknesses of the base and at least one of the flanges, wherein the first and the second arms are connected and pivotal about a joint such that the respective first and second distal ends of the first and the second arms are separable upon pivotal movement of the first and the second arms about the joint.

2. The instrument of claim 1, further comprising:
at least a first jaw attached to the first distal end and dimensioned to receive the thickness of either or both of (i) a first portion of the base and (ii) the first flange, wherein at least the pair of second jaws are dimensioned to receive the thickness of either or both of (i) a second portion of the base and (ii) the second flange.

3. The instrument of claim 2, wherein the first jaw attached to the first distal end and the pair of second jaws extending from the second distal end define first and second channels, respectively, and wherein the first and second channels face in opposite directions, and wherein the respective first and second channels receive the thicknesses of either or both of the (i) the first and second portions of the base and (ii) the first and second flanges that at least the pair of second jaws is dimensioned to receive.

4. The instrument of claim 1, wherein the first and second distal ends of the first and second arms are separable to a plurality of arm positions from each other and the pair of second jaws are moveable to a plurality of positions when the respective first and second distal ends of the first and second arms are separated by any of the plurality of arm positions.

5. The instrument of claim 1, further comprising:
a fastener attached to the second distal end, the fastener being moveable from a first position to a second position in a direction transverse to the movement of the post,
wherein the fastener is not engaged with the post in the first position of the fastener such that the post is slideable relative to the second distal end, and
wherein the fastener is engaged with the post in the second position of the fastener such that the post is not slideable relative to the second distal end.

6. The instrument of claim 5, wherein the post includes at least one notch, and wherein a distal end of the fastener is dimensioned to be received in the at least one notch to set the post at a predetermined location relative to the second distal end.

7. The instrument of claim 1, further comprising:
an adjustment mechanism for engagement with the post, wherein the post is in a first post position at a first position of the adjustment mechanism and the post is in a second post position at a second position of the adjustment mechanism.

8. The instrument of claim 1, wherein the post has a measurement marker thereon, and the measurement marker providing a marker for determining the relative location of the pair of second jaws to the second distal end.

9. An instrument for the manipulation and insertion of an osteosynthesis clip, the osteosynthesis clip including a base having at least first and second portions, a thickness, and at least first and second flanges extending from the base and having a thickness, the instrument comprising:
a first arm having a first distal end;
a second arm attached to the first arm and having a second distal end, the second distal end having a blind bore therein, the first and the second arms being connected and pivotal about a joint such that the distal ends of the first and second arms are separable to a plurality of arm positions from each other;
at least a first jaw attached to the first distal end and dimensioned to receive the thickness of either or both of (i) the first portion of the base and (ii) the first flange; and
a post including at least a pair of second jaws and being moveable within the blind bore, the pair of second jaws extending from the second distal end and being dimensioned to receive the thickness of either or both of (i) the second portion of the base and (ii) the second flange,
wherein the pair of second jaws are moveable to a plurality of positions relative to the second distal end.

10. A system for the manipulation and insertion of an osteosynthesis clip, the system comprising:
an osteosynthesis clip including a base having first and second portions, a thickness, and at least first and second flanges extending from the base, the flanges having a thickness; and
the instrument of claim 9.

11. The system of claim 10, wherein the osteosynthesis clip is a first clip, the system further comprising a second clip, wherein first and second portions of a base of the first clip are offset from each other a first distance prior to being received in the first jaw and the second jaw, respectively, and first and second portions of a base of the second clip are offset from each other a second distance different than the first distance prior to being received in the first jaw and the second jaw, respectively.

12. The system of claim 10, wherein profiles of each of the first and second flanges of the osteosynthesis clip and the first and second arms lie in the same plane when either or both of (A) (i) the first portion of the base and (ii) the first flange at least the first jaw is dimensioned to receive is received in the first jaw and (B) (i) the second portion of the base and (ii) the second flange that at least the pair of second jaws is dimensioned to receive is received in the pair of second jaws.

13. The instrument of claim 9, wherein the first jaw attached to the first distal end and the pair of second jaws extending from the second distal end define first and second channels, respectively, and wherein the first and second channels face in opposite directions, and wherein the respective first and second channels receive the thicknesses of either or both of the (i) the first and second portions of the base and (ii) the first and second flanges that at least the pair of second jaws is dimensioned to receive.

14. An instrument for the manipulation and insertion of an osteosynthesis clip, the osteosynthesis clip including a base having at least first and second portions, a thickness, and at least first and second flanges extending from the base and having a thickness, the instrument comprising:
 a first arm having a first distal end;
 a second arm attached to the first arm and having a second distal end, the first and the second arms being connected and pivotal about a joint such that the distal ends of the first and second arms are separable to a plurality of arm positions from each other within a plane;
 at least a first jaw attached to the first distal end and dimensioned to receive the thickness of either or both of (i) the first portion of the base and (ii) the first flange; and
 at least a pair of second jaws extending from the second distal end and dimensioned to receive the thickness of either or both of (i) the second portion of the base and (ii) the second flange,
 wherein the pair of second jaws are moveable to a plurality of positions relative to the second distal end, and
 wherein the first jaw attached to the first distal end and the pair of second jaws extending from the second distal end define first and second channels, respectively, and wherein the first and second channels face in opposite directions away from the plane defined by the attached first and second arms, and wherein the respective first and second channels receive the thicknesses of either or both of the (i) the first and second portions of the base and (ii) the first and second flanges that at least the pair of second jaws is dimensioned to receive.

15. The instrument of claim 14, the second distal end having a bore extending therein, further comprising a post slideable within the bore, wherein the pair of second jaws extends from the post.

16. The instrument of claim 15, further comprising:
 an adjustment mechanism for engagement with the post, wherein the post is in a first post position at a first position of the adjustment mechanism and the post is in a second post position at a second position of the adjustment mechanism.

17. The instrument of claim 14, further comprising:
 a post extendable from the second distal end, wherein the pair of second jaws is attached to the post; and
 a fastener attached to the second distal end, the fastener being moveable from a first position to a second position in a direction transverse to the movement of the pair of second jaws,
 wherein the fastener is not engaged with the post in the first position of the fastener such that the post is extendable from the second distal end, and
 wherein the fastener is engaged with the post in the second position of the fastener such that the post is not extendable from the second distal end.

18. The instrument of claim 17, wherein the post includes at least one notch, and wherein a distal end of the fastener is dimensioned to be received in the at least one notch to set the post at a predetermined location relative to the second distal end.

19. The instrument of claim 14, further comprising:
 a post extendable from the second distal end, wherein the first jaw is attached to the post; and
 an adjustment mechanism for engagement with the post, wherein the post is in a first position at a first position of the adjustment mechanism and the post is in a second position at a second position of the adjustment mechanism.

20. A system for the manipulation and insertion of an osteosynthesis clip, the system comprising:
 an osteosynthesis clip including a base having first and second portions, a thickness, and at least first and second flanges extending from the base, the flanges having a thickness; and
 the instrument of claim 14.

* * * * *